United States Patent [19]

Haugland

[11] 4,213,904

[45] Jul. 22, 1980

[54] FLUORESCENT LABELING REAGENTS CONTAINING THE FLUORESCEIN AND EOSIN CHROMOPHORES

[76] Inventor: Richard P. Haugland, 1008 Orlando Cir., Plano, Tex. 75075

[21] Appl. No.: 16,084

[22] Filed: Feb. 28, 1979

[51] Int. Cl.$^2$ ............................................. C07D 405/08
[52] U.S. Cl. ............................ 260/326.5 CA; 544/212; 260/335
[58] Field of Search ............................ 260/326.5 CA

[56] References Cited

PUBLICATIONS

Cherry et al., *Biochemistry,* vol. 15, 3653 (1976).
Kanaoka, *Angewandte Chemie,* vol. 89, p. 142 (1977).

*Primary Examiner*—John M. Ford

[57] ABSTRACT

Preparation of maleimide, haloacetamide, (3,5-dichlorotriazinyl)-amino and thiosemicarbazide derivatives of fluoroescein and eosin.

1 Claim, No Drawings

FLUORESCENT LABELING REAGENTS CONTAINING THE FLUORESCEIN AND EOSIN CHROMOPHORES

This invention relates to fluorescent labeling of biologically active molecules. More particularly it relates to improved fluorescent labeling compounds containing the fluorescein or 2′,4′,5′,7′-tetrabromofluorescein (also known as eosin) nucleus and also containing maleimide, haloacetamide, (3,5-dichlorotriazinyl)amino or thiosemicarbazide groups for attaching the fluorescent compound by covalent linkage to the biomolecule.

The concept of using synthetic organic labels and the advantages where such labels contain a fluorescent group in labeling biomolecules has been thoroughly reviewed (Kanoka, 1977). The principal object of the present invention is to provide an improved class of labels with the advantage of intense light absorption and emission which permits detectability at low concentrations in the visible part of the electromagnetic spectrum away from the region of absorption of most biomolecules. This is combined with a chemical reactivity which in certain circumstances may be specific for certain functional groups commonly found in biomolecules. One of the few fluorescent labels with spectral properties similar to those to be described in fluorescein isothiocyanate which has reactivity selective for amino groups in biomolecules. In contrast, maleimide and haloacetamide derivatives such as those to be described are usually thought to be sulfhydryl-selective, especially as the pH is lowered toward neutrality. The same is probably true of (3,5-dichlorotriazinyl)amino derivatives. As the pH is raised, these three functional groups become more reactive with amino and phenolic residues. Thiosemicarbazides are common derivatizing reagents for compounds containing aldehydes or ketones. Such functional groups are found either naturally in many biomolecules or may be introduced into ribonucleic acids, glycoproteins, mono or polysaccharides and other molecules containing vicinal diol groups by periodate oxidation.

The new fluorescent labels of this invention comprise a fluorescein ($R_1=R_2=R_3=R_4=$hydrogen atom) or eosin ($R_1=R_2=R_3=R_4=$bromine atom) nucleus chemically linked at either $R_5$ or $R_6$ to one of the following reactive groups: (2) maleimide, (3) haloacetamide (X is either a chlorine, bromine or iodine atom), (4) (3,5-dichlorotriazinyl)amino or (5) thiosemicarbazide.

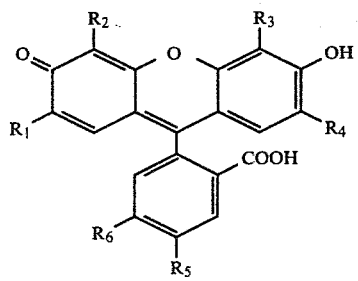

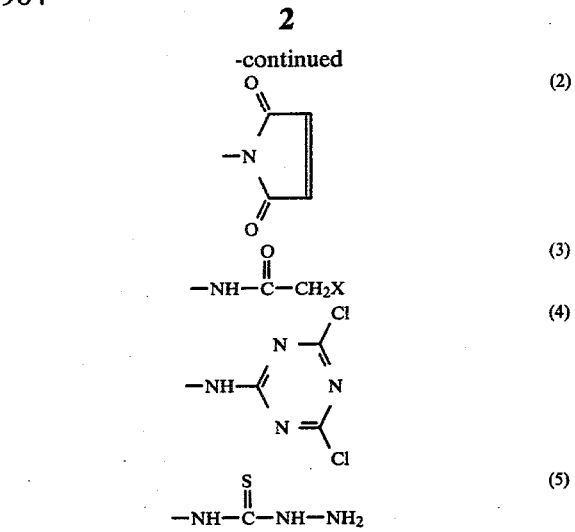

The new fluorescent labels may be prepared by straightforward synthetic techniques familiar to anyone skilled in the art. The starting materials for all syntheses are ultimately either 5-nitrofluorescein ($R_1=R_2=R_3=R_4=R_6=$a hydrogen atom; $R_5=NO_2$, a nitro group) or 6-nitrofluorescein ($R_1=R_2=R_3=R_4=R_5=$a hydrogen atom; $R_6=NO_2$). For the fluorescein labels to be described, these are reduced to the corresponding amino derivatives ($R_5$ or $R_6NH_2$, an amine group) which are commercially available. The 5-nitrofluorescein or 6-nitrofluorescein can be converted to 5-nitroeosin or 6-nitroeosin respectively by treatment with at least four equivalents of bromine in alcohol (see EXAMPLE I). These can be reduced using the same methods used for reduction of the nitrofluorescein isomers to 5-aminoeosin or 6-aminoeosin which serve as the starting materials for preparation of the eosin maleimide, haloacetamide, (3,5-dichlorotriazinyl)amino and thiosemicarbazide labels. Alternatively, the eosin labels containing haloacetamide or (3,5-dichlorotriazinyl)amino groups may be prepared from the corresponding fluorescein derivatives by treatment with four equivalents of bromine in ethanol.

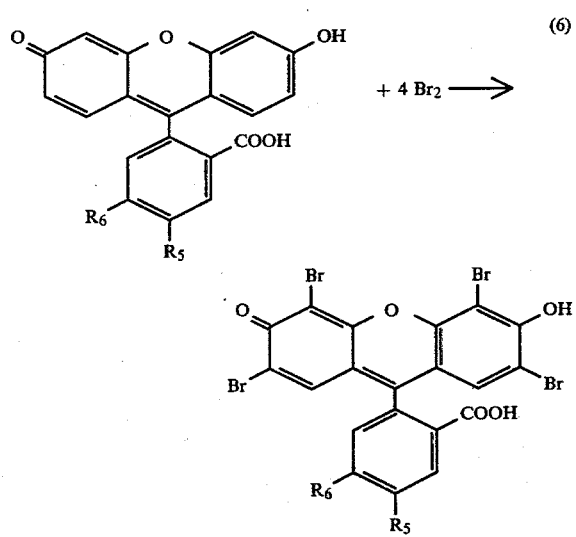

Synthesis of the maleimide derivatives of either fluorescein or eosin follows the sequence below (7) where the symbol in the brackets represents either a fluorescein or eosin group attached to the amino residue at either the $R_5$ or $R_6$ positions. The traditional ring closing reaction of maleamic acids to maleimides by acetic anhydride and sodium acetate is not useful for fluorescein and eosin derivatives due to reaction of the hydroxyl groups of the chromophore with acetic anhydride.

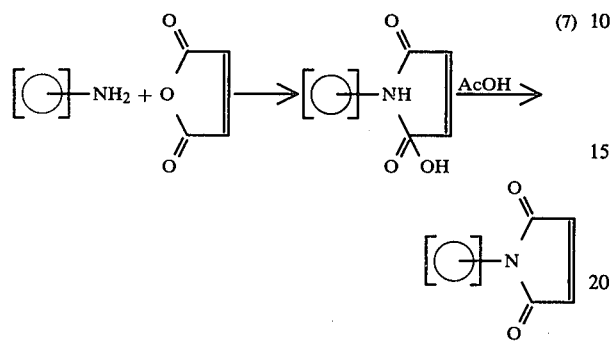

Several methods have been developed for synthesis of haloacetamide derivatives of fluorescein and eosin. The most successful is treatment of aminofluorescein or aminoeosin with chloroacetic anhydride to give the chloroacetamide (X=Cl) or bromoacetic anhydride to give the bromoacetamide (X=Br). Alternatively, the haloacetamides can be

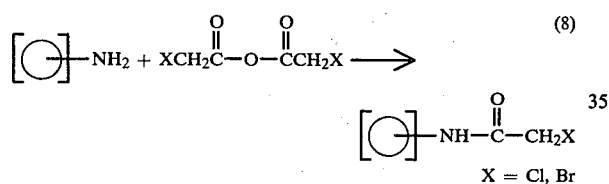

prepared using chloroacetyl chloride (X=Cl), bromoacetyl bromide (X=Br) or iodoacetyl chloride (X=I) or similar reagent using a base such as pyridine or triethylamine as acid scavenger.

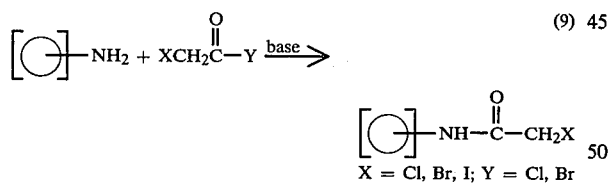

The iodoacetamide can in each case be most conveniently prepared from the chloroacetamide or bromoacetamide by an exhange reaction with an alkali iodide in a suitable solvent such as acetone or dimethylformamide.

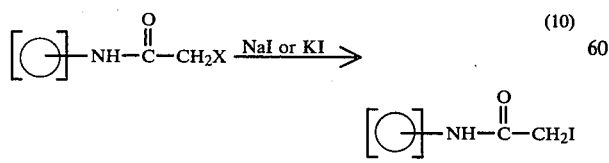

The (3,5-dichlorotriazinyl)amino derivatives have been prepared by reacting the aminofluorescein or aminoeosin with cyanuric chloride in alcohol. The eosin derivative also may be prepared from either isomer of (3,5-dichlorotriazinyl)aminofluorescein by treatment with four equivalents of bromine according to equation 6.

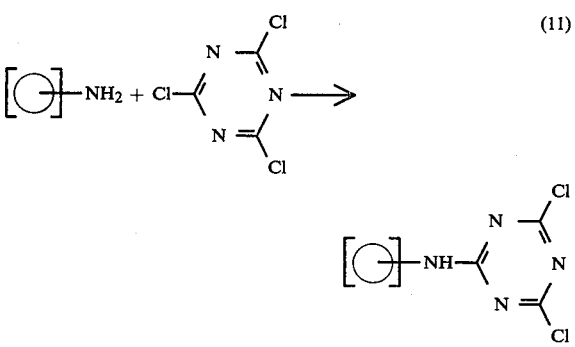

To prepare the thiosemicarbazide derivatives of fluorescein or eosin requires prior preparation of the isothiocyanates from the corresponding amines and thiophosgene. Eosin isothiocyanates can also be prepared from fluorescein isothiocyanates with four equivalents of bromine in ethanol (Cherry, et al, 1976). Treatment of the isothiocyanates with excess hydrazine in alcohol gives the thiosemicarbazides.

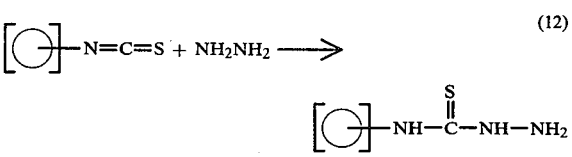

The following examples illustrate the preparation of several labels within the scope of the invention. The examples are intended to demonstrate the general methods used in the syntheses and not to limit claims under this invention. Although the synthetic procedures are described in some detail by way of illustration and for the purposes of clarity and understanding, it is understood that certain changes and modifications in procedure and reagents may be practiced within the spirit of the invention as limited only by the scope of the appended claims.

EXAMPLE I

Conversion of 5-nitrofluorescein to 5-nitroeosin (Equation 6; $R_5$=NO$_2$; $R_6$=H.)

A suspension of 1.06 g (2.81 mmole) pure 5-nitrofluorescein in 10 ml 95% ethanol was treated dropwise over 10 minutes with 1.8 ml liquid bromine with stirring. Complete solution was not obtained but thin layer chromatography (T.L.C.) using ethanol showed a single pink spot migrating ahead of 5-nitrofluorescein. The red solid was filtered, washed well with ethanol and dried yielding 2.04 g of product. Similar reactions were used to convert 6-nitrofluorescein to 6-nitroeosin, the haloacetamidofluorescein isomers to haloacetamidoesoins and the (3,5-dichlorotriazinyl)aminofluorescein isomers to (3,5-dichlorotriazinyl)aminoeosins.

EXAMPLE II

Synthesis of fluorescein maleimides and eosin maleimides (equation 7).

A solution of 5.0 g 5-aminofluorescein in 25 ml of anhydrous dimethylformamide was treated with 2.5 g solid maleic anhydride at room temperature for 30 minutes. A T.L.C. using 60:40 benzene:ethanol showed quantitative conversion of the fast-migrating and aminofluorescein to a non-migrating yellow fluorescent product. A yellow solid was precipitated by stirring the reaction mixture into 500 ml water. This was suction filtered and air dried then vacuum dried yielding 6.0 to 6.5 g of crude fluorescein-5-maleamic acid. This was dissolved in 20 ml dimethylformamide and then diluted with 60 ml acetic acid. The solution was heated at reflux until T.L.C. with 60:40 benzene:ethanol showed an insignificant amount of starting material remaining and a new fast-migrating yellow fluorescent product present (usually 3 to 4 hours). The reaction mixture was poured while hot onto 500 ml crushed ice giving a yellow to yellow-orange solid which weighed 5.0 to 5.5 g after vacuum drying. The material was sufficiently pure for use as a fluorescent probe but undergoes some ring-opening decomposition when recrystallization is attempted. The eosin maleimides were synthesized in an identical manner except that they usually precipitated from the reaction mixture during the ring-closing step.

EXAMPLE III

Synthesis of eosin-5-iodoacetamide from 5-aminoesin (equations 8 and 10).

To a solution of 1.00 g 5-aminoesoin in 10 ml anhydrous dimethylformamide was added 1.0 gm of chloroacetic anhydride all at once. A mild exotherm resulted with the color changing from red to red-orange. On T.L.C. (ethanol), the slower-migrating and non-fluorescent aminoeosin was quantitatively replaced by a yellow fluorescent faster migrating spot. The product was isolated as a dark red powder in nearly quantitative yield by precipitation with water. After vacuum drying, the chloroacetamide was dissolved in a mixture of 10 ml dimethylformamide and 25 ml acetone and 2.0 g sodium iodide was dissolved to give a complete solution. Within minutes a colorless precipitate of sodium chloride was evident. The reaction mixture was protected from light due to the known susceptibility of iodoacetamides to photodecomposition. After 48 to 72 hours at room temperature, the product was precipitated with water as a dark red solid (1.2 to 1.5 gm after vacuum drying). The bromoacetamide was prepared from aminoeosin and bromoacetic anhydride in the same manner as the chloroacetamide.

EXAMPLE IV

Synthesis of 5-(3,5-dichlorotriazinyl)aminoeosin from 5-aminoeosin (equation 11).

A solution of 1.33 g (2.00 mmole) 5-aminoeosin in 20 ml anhydrous ethanol was treated with 0.368 g (2.00 mmole) cyanuric chloride powder. Within minutes the complete red solution gave a thick precipitate which was suction filtered and washed well with ethanol. The red powder was vacuum dried at 80° to remove HCl and migrated as a single fluorescent spot on T.L.C. The identical product was also prepared from either isomer of (3,5-dichlorotriazinyl)aminofluorescein with four equivalents of bromine in ethanol suspension.

EXAMPLE V

Synthesis of fluorescein-5-thiosemicarbazide from fluorescein-5-isothiocyanate (equation 12).

Fluorescein-5-isothiocyanate (0.50 g, 1.29 mmole) was dissolved in 50 ml anhydrous ethanol containing 3 ml hydrazine hydrate. After about one hour of stirring at room temperature, a yellow precipitate suddenly formed. This was filtered and washed with ethanol yielding 0.51 g of very water soluble salt. This was dissolved in 10 ml water and precipitated by addition of dilute HCl until the pH reached 6.0. The yellow product after washing with water and vacuum drying weighed 0.40 g. On T.L.C. it migrated very slowly compared with the isothiocyanate but gave a new fast-migrating product when dissolved in acetone for 15 minutes. Eosin thiosemicarbazides and fluorescein-6-thiosemicarbazide were prepared in a similar manner from the appropriate isothiocyanates (Cherry, et al, 1976).

What is claimed is:

1. Fluorescent labels for biomolecules comprising the fluorescein or eosin chromophores covalently attached at the 5 or 6 position to the nitrogen of a maleimide group.

* * * * *